United States Patent [19]

Ku et al.

[11] Patent Number: 5,561,121
[45] Date of Patent: Oct. 1, 1996

[54] STABLE LYOPHILIZED THIOTEPA COMPOSITION

[75] Inventors: Mannching S. Ku, Rockland, N.Y.; Jorge Velez, Carolina, Puerto Rico; Rodney J. Hoffman, Bayamon, Puerto Rico; Lourdes Zamora, Guaynabo, Puerto Rico

[73] Assignee: American Cyanamid Company, Madison, N.J.

[21] Appl. No.: 284,336

[22] Filed: Aug. 2, 1994

Related U.S. Application Data

[63] Continuation-in-part of Ser. No. 150,501, Nov. 9, 1993, abandoned.

[51] Int. Cl.⁶ .................. A61K 31/675; C07D 203/06
[52] U.S. Cl. .................. 514/83; 514/970; 548/956
[58] Field of Search .................. 514/118, 110, 514/970, 83; 548/956, 969; 424/409

[56] References Cited

U.S. PATENT DOCUMENTS

| | | | |
|---|---|---|---|
| 2,670,347 | 2/1954 | Kuh et al. | 548/956 |
| 4,315,002 | 2/1982 | Maurer | 424/181 |
| 4,918,199 | 4/1990 | Kazan | 548/956 |
| 4,992,366 | 2/1991 | Buergisser | 435/35 |
| 5,122,367 | 6/1992 | Ron et al. | 424/80 |

*Primary Examiner*—José G. Dees
*Assistant Examiner*—Deborah Lambkin
*Attorney, Agent, or Firm*—Arnold S. Milowsky

[57] ABSTRACT

A stable lyophilized composition of the antitumor alkylating agent thiotepa and a method of preparing such a composition via co-lyophilization of the active ingredient with a pharmaceutical acceptable alkalizing agent.

7 Claims, No Drawings

STABLE LYOPHILIZED THIOTEPA COMPOSITION

This is a continuation-in-part of application Ser. No. 08/150,501, filed on Nov. 9, 1993, abandoned.

FIELD OF THE INVENTION

The present invention relates to a stable lyophilized composition of the-antitumor alkylating agent (N,N',N''-triethylene-phosphoramide) and a method of preparing such a composition via co-lyophilization of the active ingredient with a pharmaceutically acceptable alkalizing agent.

BACKGROUND OF THE INVENTION

Thiotepa is an ethylenimine type compound, also referred to as 1,1',1''-phosphinothioylidynetrisaziridine which has the following structure:

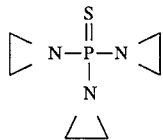

It is a polyfunctional alkylating agent used in the chemotherapy of various neoplastic diseases including adenocarcinoma of the breast and ovaries and for the treatment of superficial papillary carcinoma of the urinary bladder. Preparation of the compound is reported in U.S. Pat. Nos. 2,670,347 and 4,918,199.

At present, thiotepa is commercially provided in a pharmaceutical dosage form for parenteral use as a sterile powder for reconstitution containing a mixture of thiotepa powder, sodium chloride and sodium bicarbonate. When reconstituted with Sterile Water for Injection, the resulting solution has a pH of about 7.6. Whether in its original powder form or reconstituted, it must be stored under refrigerated conditions (2°–8° C.). The reconstituted solution is only stable for about 5 days as a reconstituted solution, even under refrigerated conditions.

The thiotepa sterile powder is known to degrade rapidly to a hazy solution upon reconstitution with aqueous media. It is theorized that the haze is due to a polymerization reaction which occurs when the compound is exposed to water. It is known that as thiotepa bulk degrades, water is consumed, and a decrease of water content can be detected. It has also been reported that the solution is more stable at an alkaline pH.

Several attempts have been made to stabilize the thiotepa composition and slow down or prevent the haze formation that occurs in aqueous media. Sodium bicarbonate was added to the powder formulation as a stabilizer based on the theory that the presence of the bicarbonate would render the environment of the powder alkaline and stabilize the thiotepa via a pH mechanism. However, contrary to this theory, the data indicated that the presence of sodium bicarbonate in the sterile powder did not stabilize thiotepa and prevent the rapid haze formation.

Thus, there is a need for a formulation of thiotepa which has improved stability and which does not undergo such rapid haze formation upon reconstitution with aqueous media.

It is known in the art that freeze-drying (lyophilization) of a product which is relatively unstable in aqueous solution can result in a product that is stabilized and therefore has a longer shelf life than an aqueous solution Additionally, a freeze-dried product has an advantage over a product in powder form in that it is rapidly soluble and easily reconstituted prior to administration by injection. Another advantage of freeze-drying a product unstable in aqueous solution is that it can be processed and filled into dosage containers in a liquid state, dried at low temperatures thereby eliminating adverse thermal effects, and stored in the dry state where it may be more stable. (See Remington's Pharmaceutical Sciences, 15th edition, pp. 1483–1485 (1975)). Thus, freeze-drying would be an ideal method of obtaining a formulation of thiotepa which would exhibit the improved stability.

However, the present inventors have found that lyophilization of an aqueous solution of thiotepa did not result in an appreciable improvement in stability or an appreciable decrease in haze formation upon reconstitution.

SUMMARY OF THE INVENTION

It is an object of the present invention to provide a thiotepa composition which exhibits improved stability and which does not exhibit rapid haze formation in aqueous media.

It is also an object of the present invention to provide a method of preparing a thiotepa composition for improved stability.

It is also an object of the present invention to provide a thiotepa composition that is rapidly soluble and easily reconstituted prior to administration by injection.

These and other objects and advantages are accomplished with the present invention which comprises a thiotepa composition for parenteral administration prepared by co-lyophilizing thiotepa with a pharmaceutically acceptable base such that the composition has a pH of 7–9 upon reconstitution with an aqueous diluent. Surprisingly, it has been found that the addition of a pharmaceutically acceptable base to the thiotepa composition prior to lyophilization yields a project which exhibits greatly improved stability and reduced haze formation when reconstituted with aqueous media.

The "pharmaceutically acceptable base" may be selected from any pharmaceutically acceptable substance whose molecules can take up protons but is not a nucleophile such as sodium bicarbonate, potassium bicarbonate, sodium carbonate, sodium phosphate and sodium hydroxide.

In accordance with the process of the present invention, an improved thiotepa composition is prepared by adding the pharmaceutically acceptable base to thiotepa aqueous solution to obtain a pH of the solution titrated to a level of 7–9. The resulting solution is then freeze dried using conventional freeze drying techniques. The resulting product exhibits much reduced haze formation upon reconstitution.

DETAILED DESCRIPTION

Without being bound by any particular theory of the invention, it is postulated that the co-lyophilization of the pharmaceutically acceptable base with the thiotepa results in deposition of the base on the surface of thiotepa crystals to effect an alkaline microenvironment which slows down the proton facilitated polymerization of the thiotepa solution. This would explain the surprising finding that the solid mix of thiotepa powder with the base failed to slow down the haze formation whereas the addition of the base to the solution prior to freeze drying resulted in a product which exhibits reduced haze formation. Accordingly, the present invention is an improvement in the process for preparing a freeze dried thiotepa composition for parenteral administration, the improvement comprising the addition of an acceptable amount of pharmaceutically acceptable base prior to freeze drying to facilitate the intimate contact of the base with thiotepa crystals, forming a protective envelope of base around the thiotepa molecule.

A description of the thiotepa active ingredient of the present invention are described in the aforementioned U.S. Pat. Nos. 2,670,347 and 4,918,199 hereby incorporated by reference into the present application.

In accordance with the present invention, the freeze-dried thiotepa preparation is manufactured from a bulk concentrate of thiotepa in aqueous solution. The bulk concentrate of thiotepa has a pH of around 6.0. A separate aqueous solution of pharmaceutically acceptable base at a higher concentration relative to thiotepa bulk solution is added to the bulk solution of thiotepa to raise the pH of the resulting solution to a level of 7–9, preferably 8–9. The solution is then sterile filtered and filled into vials and freeze dried. Preferably, the freeze drying is done under the following conditions:

Freezing cycle: −30° C. for at least 2 hours

Primary drying: heat shelf at 2° C./hour from −30° C. to 0° C.

Secondary drying: maintain product temperature at about 6° C. for at least 3 hours.

Break vacuum with dry filtered nitrogen. Preferably, the freeze-drying is conducted under a constant vacuum between 900 and 1000 μm throughout the cycle. The resulting product is then preferably stored under refrigerated conditions. Prior to administrating the preparation to a patient, the freeze-dried product is reconstituted with a pharmaceutically acceptable diluent such as Sterile Water for Injection.

It is contemplated that other ingredients may be included in the formulation of the product of the present invention. These may include wetting or emulsifying agents, antimicrobial agents or preservatives, as necessary. Also, non-electrolyte, non-nucleophilic bulking agents such as mannitol, dextrose, sucrose or dextron may be included to improve the characteristics of the freeze-dried cake. Many variations of the above, along with other suitable vehicles will suggest themselves to those skilled in the art in light of the foregoing detailed description. All such obvious variations are contemplated to be within the scope of the appended claims.

The following examples display the manufacture of the composition and a comparison of the freeze dried preparation of the present invention with a formulation freeze dried without alkalizing agent. The examples are not to be construed as limiting the scope of the invention set forth in the claims.

EXAMPLE 1

A solution of 0.5 L of filtered sterile aqueous solution of thiotepa at a concentration of 20 mg/ml is titrated to a pH of 7 with an aqueous solution of sodium bicarbonate at a concentration of 10 g in 120 ml. The solution is filled in vials while maintaining the bulk solution in an ice bath. The vials are loaded into a freeze dryer where they are kept frozen overnight at a temperature of −40° C. The vials are freeze dried with the following conditions:

freezing cycle: −30°' for at least 2 hours primary drying: heat shelf at 2° C./hour from −30° to 0° C.

secondary drying: maintain product temperature at about 6° C. for at least 3 hours. Break vacuum with dry filtered nitrogen.

EXAMPLE 2

The freeze dried preparation of the invention is prepared according to the procedure of Example 1 substituting sodium carbonate for the sodium bicarbonate in Example 1.

EXAMPLE 3

Table I shows the results of potency determination analysis following an HPLC method for compositions of the present invention.

Table II shows the clarity analysis of the reconstituted thiotepa solution of the present invention.

TABLE I

Potency Stability of Lyophilized Thiotepa Vial at 23 ± 2° C. Storage

| Label Claim: | 15 mg Thiotepa per vial. |
| Actual Target: | 15.6 mg thiotepa per vial; 104% of label claim. |
| Manufacturing: | 0.78 ml of 20 mg/ml thiotepa sterile solution was filled into vials and lyophilized. |

Thiotepa Potency (% Labelled Claim)

|  | Initial | 1 Month | 2 Month |
| --- | --- | --- | --- |
| Control pH 5.7 | 103.0 | 99.9 | 101.3 |
| NaHCO$_3$ pH 8 | 101.1 | 97.8 | 96.8 |
| Na$_2$CO$_3$ | 104.6 | 100.6 | 101.3 |
| NaHCO$_3$ Low pH 7 | 104.0 | 100.6 | 97.4 |
| Control/Holding* | 104.7 | 101.9 | 100.8 |
| NaHCO$_3$ High/Holding | 106.3 | 105.2 | 100.6 |
| Na$_2$CO$_3$/Holding | 105.4 | 104.2 | 99.0 |
| NaHCO$_3$ Low/Holding | 106.2 | 101.2 | 97.9 |

*Holding of bulk solution was done for 24 hours in a 10° C. circulating bath.

TABLE II

Clarity of Reconstituted Solution of Lyophilized Thiotepa Vial at 25 ± 2° C.

| Label Claim: | 15 mg Thiotepa per vial. |
| Actual Target: | 15.6 mg thiotepa per vial; 104% of label claim. |
| Manufacturing: | 0.78 ml of 20 mg/ml thiotepa sterile solution was filled into vials and lyophilized. For some batches, the bulk solution was held for a period of time simulating worst product condition. |
| Test Procedure: | Five lyophilized thiotepa vials were reconstituted with Water for Injection and clarity of the reconstituted solution was determined as clear (−), slightly hazy (+), hazy (++) or very hazy (+++). At 2 month, only three vials were checked due to sample availability. |

Clarity of the Reconstituted Solution**

| Pilot Batch | Initial | 1 Week | 2 Week | 3 Week | 1 Month | 2 Month |
| --- | --- | --- | --- | --- | --- | --- |
| Control pH 5.7 | − | + | ++ | ++ | ++ | ++ |
| NaHCO$_3$ High pH 8 | − | − | − | − | − | + |
| Na$_2$CO$_3$ | − | − | − | − | − | + |
| NaHCO$_3$ Low pH 7 | − | − | − | − | − | ++ |
| Control/Holding* | − | + | + | ++ | ++ | +++ |
| NaHCO$_3$ High/Holding | − | − | − | − | − | +++ |
| Na$_2$CO$_3$/Holding | − | − | − | − | − | ++ |
| NaHCO$_3$ Low/Holding | − | − | − | − | + | ++ |

*Holding of bulk solution was done for 24 hours in a 10° C. circulating bath.

We claim:

1. A freeze-dried thiotepa composition for parenteral administration which comprises:
thiotepa and sufficient pharmaceutically acceptable base to render the pH of an aqueous solution containing said solution from pH 7–9.

2. In a process for preparing a freeze dried thiotepa composition, the improvement which comprises adding an acceptable amount of a pharmaceutically acceptable base prior to freeze drying the composition to facilitate the intimate contact of the base with thiotepa crystals.

3. A composition according to claim 1, wherein the pharmaceutically acceptable base is selected from sodium bicarbonate and sodium carbonate.

4. A process according to claim 2, wherein the pharmaceutically acceptable base is selected from sodium bicarbonate and sodium carbonate.

5. A composition according to claim 1, which consists essentially of the freeze dried composition of claim 1, in association with a pharmaceutically acceptable excipient.

6. A composition according to claim 5, in which the pharmaceutically acceptable excipient is a non-electrolyte bulking agent.

7. A composition of claim 6, wherein the non-electrolyte bulking agent is selected from mannitol and dextrose.

* * * * *